United States Patent [19]

Ríos

[11] Patent Number: 4,542,026

[45] Date of Patent: Sep. 17, 1985

[54] METHOD OF TREATING VASOMOTOR DISORDERS

[76] Inventor: Jose Ríos, 930 Park Ave., Elizabeth, N.J.

[21] Appl. No.: 490,174

[22] Filed: Apr. 29, 1983

[51] Int. Cl.$^4$ ............................................. A61U 31/44
[52] U.S. Cl. ................................. 514/345; 514/899; 514/870; 514/871
[58] Field of Search ........................................ 424/263

[56] References Cited

PUBLICATIONS

Chem. Abst.: 11216u, vol. 82, (1975).
Merck Index, 9th Ed., (1976), pp. 1035–1036.
Chem. Abst. 85-171902, (1976).
Chem. Abst. 68-1955F, (1965).
Dispensatory 25th, p. 1148.
Anon. "Tryptophan–Natural Alternative to Tranquilizers", reprinted from Bestways Magazine, Oct. 1981.
Anon. Clinical Pharmacology, "Pyridoxine Hydrochloride Injection USP".
Anon. Primary Cardiology, "Carcinoid Tumors, Carcinoid Syndrome and Carcinoid Heart Disease", vol. 8, No. 4, Apr. 1982.
Anon. Time Magazine, "Unlocking Pain's Secret", pp. 58–66, Jun. 11, 1984.
Anon. "Vitamin B$_6$: The Doctor's Report", (excerpts).
Anon. "Migraine The Terrible Headache", published 1971.
Anon. Your Health & Fitness "Help for Headaches", Oct.–Nov. 1983, pp. 3–7.
Drug Therapy "Migraine: New Approaches to an Old Problem", A. P. Friedman, M.D., pp. 143–146, (1984).
Anon. Red Book Magazine, "About Those Headaches", Mar. 1981, pp. 54, 56 & 58.

*Primary Examiner*—Stanley J. Friedman
*Attorney, Agent, or Firm*—Ronald G. Goebel

[57] ABSTRACT

An agent and method for treating vasomotor disorders, particularly migraine and menstrual pain is provided wherein the method comprises administering to said patient, intravenously or orally, an effective dose of the agent according to the invention, Vitamin B$_6$. The effective dose of vitamin B$_6$ is at least about 100 mg., preferably at least about 300 mg. and most preferably at least about 400 mg. Vitamin B$_2$ may also be administered for particularly effective results.

17 Claims, No Drawings

METHOD OF TREATING VASOMOTOR DISORDERS

BACKGROUND OF THE INVENTION

This invention is concerned with a method for treating vasomotor disorders, particularly migraine and menstrual pain with certain doses of Vitamin $B_6$.

Vasomotor disorders are those disorders which have an effect on the caliber of blood vessels such as the contraction and dilation of capillaries. Typical of such vasomotor disorders are menstrual pain, high blood pressure and migraine. Menstrual pain generally occurs in the lower back and abdomen before and during menstruation and is often accompanied by vomiting and headache. Migraine, also called a sick headache, is a headache, usually severe, often limited to one side of the head and sometimes accompanied by nausea and vomiting. Although the cause of migraine is not completely understood, migraine is believed to be a vasomotor disorder involving constriction and then dilation of the cerebral arteries. The pressure caused by the dilation of the arteries is transmitted to the nerves which causes severe pain. It is also thought to have a psychologic aspect since it occurs most often in persons with particular types of personalities and often follows emotional disturbances. Migraine tends to run in families and in women the headaches often occur during the menstrual periods. Abdominal migraine is a species of migraine in which abdominal symptoms are prominent. The symptoms of migraine vary greatly not only from person to person but also from time to time in the same person. The headaches are usually intense. A typical migraine attack begins with changes in vision, such as flickering before the eyes, flashes of light, or a blacking out of part of the sight.

Aspirin is usually of little help in relieving migraine. Ergotamine tartrate is quite effective but has side effects, and weekly dosages must be limited. Psychotherapy may also help to release the tensions that may be an underlying cause.

In the past treatments of vasomotor disorders such as migraine and menstrual pain have generally addressed a symptom of the disorder rather than the cause. The treatment of menstrual pain has involved the use of analgesics, diuretics and hormones. In the case of migraine, the treatment has been the use of vasoconstriction agents and beta blockers. Vasoconstriction agents such as ergotamine tartrate act to constrict the dilated arteries from their dilated condition and thus relieve the pain of migraine. Such agents provide some relief but are not fast acting and the relief provided lasts from a few hours to a few days. The patient can either take the vasoconstriction agent when a migraine attack is upon him or take it constantly to avoid attacks. Beta blockers such as Inderal (propranolol hydrochloride, trademark of Ayerst Labs, Inc.) act to prevent dilation of arteries to avoid migraine pain but have side effects and weekly dosages must be limited. In addition ergotamine tartrate cannot be used by patients having hypertension or by pregnant women.

The present invention, in contrast to the prior agents for treatment of vasomotor disorders, particularly migraine, treats the cause of migraine, that is, the imbalance between dilation and constriction of the arteries and acts to maintain that balance. In addition, there are no side effects or harmful long range effects on the patient even for large doses. Most importantly, treatment of the migraine patient using the agent is highly effective.

SUMMARY OF THE INVENTION

The agent for treatment of vasomotor disorders according to the invention is Vitamin $B_6$ in certain large dosages. Vitamin $B_6$ or pyridoxine is a water soluble vitamin found in foods and essential in small quantities for growth, health and the preservation of life itself. It is essential for the metabolism of proteins, carbohydrates and fats. Vitamin $B_6$ deficiency can cause convulsions, lethargy, menstrual changes and retardation, inflamation of the skin and anemia. Vitamin $B_6$ has never been used before for the treatment of vasomotor disorders, particularly migraine.

The patient suffering from the disorder is treated according to the invention by administering Vitamin $B_6$ intravenously or orally in dosage amounts of at least about 100 mg., the dosage being higher in the case of oral administration than in the case of intravenous administration, all other factors being equal. Vitamin $B_2$ may also be administered with $B_6$ for effective results.

DETAILED DESCRIPTION OF THE PREFERRED EMBODIMENTS

Intravenous administration of Vitamin $B_6$ to a patient suffering from migraine or other vasomotor disorder is the preferred means of administration because it achieves the fastest results in terms of relief. The Vitamin $B_6$ is dissolved in water, and injected into the patient intravenously as an aqueous solution. It has been found that generally daily injections of the vitamin $B_6$ solution are required over a period of 3 to 6 days although in many cases the patient responds soon after the first injection. The intravenous dose should be at least 100 mg. and preferably at least 300 mg.; the most preferred intravenous dose is about 400 mg. There is no definite upper limit of intravenous dosage of Vitamin $B_6$. What the body cannot assimilate it will pass as waste products and urine. Intravenous dosages greater than about 400 mg. however appear to achieve no additional benefits to the patient. The minimum dosage will vary in each patient depending on the chronicity or intensity of the vasomotor disorder. Most patients will respond well to a dosage of about 400 mg. given daily for about 3 days. Often patients respond using intravenous doses of 400 mg., each 45 minutes to an hour apart. It is also preferred to couple intravenous administration with oral administration of Vitamin $B_6$ in dosages varying from 250 mg. to 500 mg. of solid Vitamin $B_6$ twice a day. In addition Vitamin $B_2$ in dosages of from about 250 mg. to 500 mg. a day may also be given to achieve the intended results. The intravenous and oral administration is continued from 2 to 3 weeks to 2 to 3 months to effect substantially permanent relief from migraine with little or no recurrence of attacks. The dosage, frequency of administration, response to the medication and recurrence of the attacks vary in each patient according to the patient's metabolic condition. Some patients respond to one course of treatment and in others the episodes of migraine recur and the maintenance dosage has to be reinforced by intravenous administration of Vitamin $B_6$.

There are generally no adverse reactions using vitamin $B_6$ except transient and mild somnolence which was developed in one patient treated. In this case the intravenous administration was discontinued and the oral dose was diminished to 100 mg. a day. The patient recovered his alertness in a few hours. In the treatments according to the invention, other vitamins can also be administered, in particular, Vitamin B, C and folic acid.

After the symptoms disappear a maintenance treatment may be continued by administering Vitamin $B_6$ orally at dosage levels of about 500 mg. per day for 2 to 3 weeks.

In the case of angina pectoris, for example, as the vasomotor disorder the recurrency of attacks are diminished and the use of coronary vasodilators can be used less frequently with Vitamin $B_6$ administration according to the invention. Two patients were treated by Vitamin $B_6$ administration in who the coronary fload was not seriously compromised by the arteriosclerotic process.

A case of Cushing's syndrome and a case of polymiositis who were previously treated with large dosages of corticosteroids (prednisone) for over 3 years, had the swelling of their face and hands reduced in less than two months taking Vitamin $B_6$ according to the invention. The patients' general condition improved and 50% of the swelling of their face and extremities disappeared. Because vitamin $B_2$ intervenes in the metabolization of Vitamin $B_6$ in these treatments high doses of riboflavin (Vitamin $B_2$) were also given. The best results were obtained when Vitamin $B_2$ is given at a dosage of 250 mg. or more orally every day in one or divided doses.

In a case of menstrual pain wherein the patient suffered from pre-menstrual and menstrual pain, nervous tension, headache, nausea, and vomiting the treatment consisted of administering 500 mg. of Vitamin $B_6$ orally and 250 mg. of Vitamin $B_2$ orally once a day starting about 10 days prior to menstruation. By carrying out this procedure, the patient's symptoms disappeared almost completely.

In accordance with the invention, fifteen patients suffering from migraine were treated by administering Vitamin $B_6$ according to the following procedure:

Each patient was given between 300 mg. and 400 mg. of Vitamin $B_6$ intravenously depending on the chronicity or intensity of the disease; once daily for from 3 to 6 consecutive days until the symptoms disappeared. At the same time oral administration of Vitamin $B_6$ was given in a dosage varying from 250 mg. to 500 mg. twice a day and oral doses of vitamin $B_2$ of from 250 mg. to 500 mg. per day were also given.

The intravenous and oral administration was continued for about 2½ weeks. No patient complained of recurring migraine attacks thereafter.

I claim:
1. A method of treating a patient suffering from a vasomotor disorder comprising administering to said patient an effective dose of Vitamin $B_6$.
2. The method of claim 1 wherein said Vitamin $B_6$ is administered intravenously.
3. The method of claim 1 wherein said Vitamin $B_6$ is administered orally.
4. The method of claim 1 wherein said vasomotor disorder is migraine.
5. The method of claim 1 wherein said dosage is at least about 100 mg.
6. A method of treating a patient suffering from a vasomotor disorder comprising administering to said patient Vitamin $B_6$ in a dosage of at least 100 mg. at periodic intervals until relief of said disorder is achieved.
7. The method of claim 6 wherein said Vitamin $B_6$ is administered intravenously.
8. The method of claim 6 wherein said Vitamin $B_6$ is administered orally.
9. The method of claim 6 wherein said vasomotor disorder is migraine.
10. The method of claim 6 wherein said dosage is at least about 300 mg.
11. The method of claim 6 wherein said dosage is at least about 400 mg.
12. The method of claim 6 which further comprises administering Vitamin $B_2$ to said patient.
13. A method for treating a patient suffering from migraine comprising:
   (a) administering Vitamin $B_6$ to said patient intravenously at a dosage of at least 300 mg until relief of said migraine is achieved; and
   (b) administering an effective dose of Vitamin $B_6$ to said patient orally to maintain relief of said migraine.
14. The method of claim 13 wherein the amount of Vitamin $B_6$ orally administered to said patients varies from about 250 mg. to 500 mg.
15. The method of claim 12 which further comprises administering Vitamin $B_2$ to said patient.
16. The method of claim 14 wherein the amounts of Vitamin $B_2$ administered to said patients is from 250 mg. to 500 mg.
17. A method for treating a patient suffering from migraine comprising administering Vitamin $B_6$ to said patient intravenously at a dosage of at least 300 mg until relief of said migraine is achieved.

* * * * *

UNITED STATES PATENT AND TRADEMARK OFFICE
CERTIFICATE OF CORRECTION

PATENT NO. : 4,542,026
DATED : September 17, 1985
INVENTOR(S) : JOSE RIOS

It is certified that error appears in the above-identified patent and that said Letters Patent is hereby corrected as shown below:

Column 4, lines 2 and 3, delete "a vasomotor disorder" and substitute -- migraine -- therefor, insert -- intraveneously -- between "comprising" and "administering".

Column 4, lines 5 through 10 comprising claims 2 through 4 should be deleted.

Column 4, lines 13 and 14, "6." should read -- 3. --, delete "a vasomotor disorder" and substitute -- migraine -- therefor, insert -- intraveneously -- between "comprising" and "administering", line 16, delete "disorder" and substitute "migraine" therefor.

Column 4, lines 18 through 23 comprising claims 7 through 9 should be deleted.

Column 4, line 24, "10." should read -- 4. -- claim reference numeral "6" should read -- 3 --.

Column 4, line 25, "11." should read -- 5 -- claim reference numeral "6" should read -- 3 --.

Column 4, line 28, "12." should read -- 6 -- claim reference numeral "6" should read -- 3 --.

Column 4, line 30, "13." should read -- 7 --, line 33, "300 mg" should read "100 mg".

Column 4, line 38, "14." should read -- 8 --, claim reference numeral "13" should read -- 7 --.

UNITED STATES PATENT AND TRADEMARK OFFICE
CERTIFICATE OF CORRECTION

PATENT NO. : 4,542,026

DATED : September 17, 1985

INVENTOR(S) : Jose Rios

It is certified that error appears in the above-identified patent and that said Letters Patent is hereby corrected as shown below:

```
Column 4, line 41, "15." should read -- 9 --, claim reference
numeral "12" should read -- 7 --.

Column 4, line 43, "16." should read --10 --, claim reference
numeral "14" should read -- 9 --.

Column 4, line 46 "17." should read -- 11 --.

On the title page "17 Claims, No Drawings" should read
              --11 Claims, No Drawings--.
```

Signed and Sealed this

Seventeenth Day of December 1985

[SEAL]

Attest:

DONALD J. QUIGG

Attesting Officer

Commissioner of Patents and Trademarks